United States Patent [19]

Chan

[11] 4,382,954
[45] May 10, 1983

[54] FUNGICIDAL N-1-SUBSTITUTED CYCLOPROPYL-N-ACYL-2,6-DIALKYLANILINE

[75] Inventor: David C. K. Chan, Petaluma, Calif.

[73] Assignee: Chevron Research Company, San Francisco, Calif.

[21] Appl. No.: 343,087

[22] Filed: Jan. 27, 1982

[51] Int. Cl.³ .................... A01N 43/08; A01N 53/00; C07C 103/46; C07C 103/49; C07C 103/66

[52] U.S. Cl. .................... 424/285; 424/309; 424/317; 424/324; 549/496; 560/9; 560/45; 560/47; 560/48; 562/426; 562/455; 562/456; 562/457; 564/154; 564/155; 564/158

[58] Field of Search .................... 560/43, 16, 9, 48, 45, 560/47; 424/309, 285, 317, 324; 562/433, 455, 457, 426, 456; 564/158, 154, 155; 549/496

[56] References Cited

U.S. PATENT DOCUMENTS

| | | | |
|---|---|---|---|
| 3,598,859 | 8/1971 | Yates et al. | 560/43 |
| 4,098,895 | 7/1978 | Hubele et al. | 564/158 |
| 4,151,299 | 4/1979 | Hubele | 564/158 |
| 4,243,819 | 1/1981 | Henrick et al. | 560/43 |
| 4,284,791 | 8/1981 | Lunkenheimer et al. | 560/43 |
| 4,287,210 | 9/1981 | Eckhardt et al. | 560/43 |
| 4,313,957 | 2/1982 | Abblard et al. | 560/9 |

FOREIGN PATENT DOCUMENTS 2921509 11/1979 Fed. Rep. of Germany ...... 424/324

*Primary Examiner*—Natalie Trousof
*Assistant Examiner*—Patricia M. Scott
*Attorney, Agent, or Firm*—D. A. Newell; T. G. De Jonghe; L. S. Squires

[57] ABSTRACT

Compounds represented by the formula

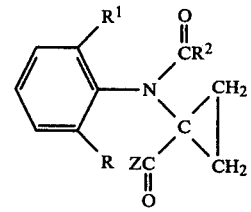

wherein R and $R^1$ are independently hydrogen or lower alkyl; $R^2$ is lower alkenyl, lower alkynyl or —$CH_2X$ wherein X is halogen, hydroxyl, lower alkoxy, lower alkylthio or a furanyl ring; and Z is hydroxyl, lower alkoxy or —$NR^3R^4$ wherein $R^3$ and $R^4$ are independently hydrogen or lower alkyl possess fungicidal activity. Moreover, some of the compounds of this invention also possess herbicidal activity.

9 Claims, No Drawings

FUNGICIDAL N-1-SUBSTITUTED CYCLOPROPYL-N-ACYL-2,6-DIALKYLANILINE

BACKGROUND OF THE INVENTION

This invention pertains to novel fungicidal compounds.

As the world becomes more dependent for food on an ever-decreasing acreage of farmland, effective fungicides which protect crops from fungicidal destruction are becoming increasingly important.

EP-28-011 discloses N-aryl-N-acyl homoserine derivatives possessing microbiodal activity.

U.S. Pat. Nos. 4,034,108 and 4,032,657 disclose N-(1'-methyl-carbalkoxymethyl)acetanilides having fungicidal activity. U.S. Pat. No. 4,151,299 discloses N-(1'-methyl-carbalkoxy)-1-alkoxy-acetanilides having fungicidal activity.

SUMMARY OF THE INVENTION

The N-1-substituted cyclopropyl-N-acyl-2,6-dialkylanilines of this invention are represented by the formula

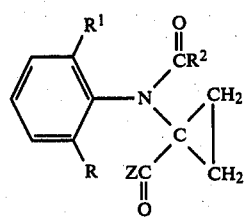

wherein R and $R^1$ are independently hydrogen or lower alkyl; $R^2$ is lower alkenyl, lower alkynyl, or $-CH_2X$ wherein X is halogen, hydroxyl, lower alkoxy, lower alkylthio or a furyl group; Z is hydroxyl, lower alkoxy or $-NR_3R_4$ wherein $R^3$ and $R^4$ are independently hydrogen or lower alkyl.

I have now found that N-1-substituted cyclopropyl-N-acyl-2,6-dialkylanilines are surprisingly effective fungicides. Moreover, some of the compounds of this invention also possess herbicidal activity.

Preferred R and $R^1$ lower alkyl groups include for instance methyl, ethyl, isopropyl and the like. Due to their superior fungicidal activity, particularly preferred compounds of this invention are those where R and $R^1$ are methyl.

Preferred $R^2$ lower alkenyl includes the 1-allyl and 2-allyl groups.

Preferred Z groups are hydroxy, methoxy, and dimethylamino. Due to its superior fungicidal activity, a particularly preferred Z group is methoxy.

DEFINITIONS

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-hexyl, and the like.

The term "alkenyl" refers to unsaturated alkyl groups having a double bond [e.g., $CH_3CH=CH(CH_2)_2-$] and includes both straight- and branched-chain alkenyl groups. "Lower alkenyl" refers to groups having a total of from 2 to 6 carbon atoms. Typical lower alkenyl groups include, for example, ethylene, but-3-enyl, hex-4-enyl, 2-methylpent-4-enyl, and the like.

The term "halo" or "halogen" refers to the groups fluoro, chloro, bromo and iodo.

The term "alkoxy" refers to the group $R^7O-$ wherein $R^7$ is alkyl. The term "lower alkoxy" refers to alkoxy groups having from 1 to 6 carbon atoms; examples include methoxy, ethoxy, hexoxy, and the like.

The term "alkynyl" refers to unsaturated alkyl groups having a triple bond [e.g. $CH_3C\equiv C(CH_2)_2-$] and includes both straight- and branched-chain alkynyl groups.

The term "lower alkynyl" refers to alkynyl groups having from 2 through 6 carbon atoms and includes, for example, but-3-ynyl; hex-4-ynyl; 4-methylpent-2-ynyl and the like.

The term "alkylthio" refers to the group $R^6S-$ where $R^6$ is alkyl. The term "lower alkylthio" refers to the group $R^6S-$ where $R^6$ is lower alkyl.

The term "furanyl group" refers to the ring

where substitution may be either at the 2 or 3 position

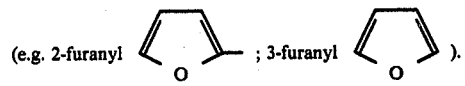

The term "carbonyl" refers to the group $>C=O$.
The term "hydroxycarbonyl" refers to the group

The term "alkoxycarbonyl" refers to the group

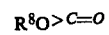

wherein $R^8$ is lower alkyl.

DETAILED DESCRIPTION OF THE INVENTION

The compounds of the present invention are preferably prepared according to the following scheme:

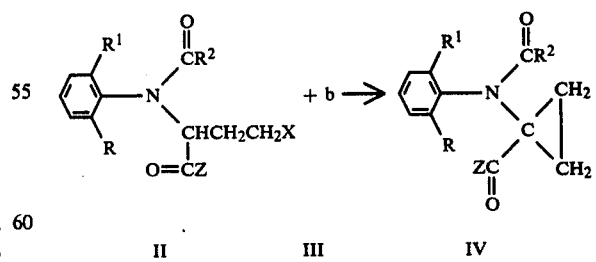

where R, $R^1$, $R^2$ and Z are as defined above, X is a halogen and b represents either an organic or an inorganic base. The synthesis of the starting 1-(2'-haloalkyl)-carbalkoxymethyl-substituted acetanilide (II) is reported in my copending United States application, Ser. No. 280,653, which is incorporated herein by reference.

The above reaction is conducted by adding an essentially equimolar amount of a base to the 1-(2'-haloalkyl)-carbalkoxymethyl-substituted-acetanilide (II) starting material. The base employed may either be an organic or an inorganic base. Suitable organic bases include for instance 1,5-diazabicyclo[4.3.0]-nonene-5(DBN), lithium diisopropyl amide (LDA), and the like. Suitable inorganic bases include for instance sodium alkoxides, sodium hydroxide, sodium hydride and the like. The reaction is conducted in the liquid phase employing an inert organic solvent such as dimethoxyethane, benzene, toluene, and the like. Preferably the reaction employs sodium hydride as the base and dimethoxyethane as the solvent. In order to facilitate reaction completion and to improve the overall yield, a catalytic amount of an organic alcohol such as methanol or ethanol is sometimes necessary. The reaction is generally conducted at from 0° to 100° C. although preferably at from 18° to 50° C. Reaction pressure is not critical and for convenience the reaction is generally conducted at atmospheric pressure. The reaction is generally complete within 1 to 120 hours. The product, IV, is then isolated and purified by conventional procedures such as extraction, filtration, chromatography, distillation and the like.

The esters of formula I are converted to the corresponding carboxylic acids of this invention by acid or base hydrolysis using conditions well known in the art.

The amido compounds of this invention (i.e. $Z=-NR^3R^4$) are prepared by reacting an essentially equimolar amount of the carboxylic acid (i.e. $Z=OH$) with a reagent capable of converting a carboxylic acid to an acid halide. Suitable reagents include, for example, thionyl chloride, oxayl chloride and the like. The reaction is done in the liquid phase using an inert organic solvent such as diethyl ether, tetrahydrofuran and the like. Reaction pressure is not critical and for convenience the reaction is generally conducted at atmospheric pressure. The reaction is generally conducted at from 0° to 100° C. and is generally complete from within 1 to 24 hours.

The acid halide is then converted to the amido compounds of this invention by addition of 2 equivalents of the appropriate amine, $HNR^3R^4$ where $R^3$ and $R^4$ are as defined above. The reaction is conducted in the liquid phase using an inert organic solvent such as chloroform, toluene and the like. Excess amine is employed to scavenge the acid generated in the reaction. Reaction pressure is not critical and for convenience the reaction is generally conducted at atmospheric pressure. The reaction is generally conducted at from 0° to 100° C. and is generally complete from within 1 to 24 hours. The product is then isolated and purified by conventional procedures such as extraction, filtration, distillation, chromatography and the like.

UTILITY

The compounds of the present invention are useful for controlling fungi. In particular, some of the compounds of this invention are useful for controlling leaf blights caused by organisms such as *Phytophthora infestans conidia, alternaria solani conidia, septoria apii* and downy mildew caused by organisms such as *Plasmopara viticola*.

However, some fungicidal compounds of the invention may be more fungicidally active than others against particular fungi. Table II lists a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, organic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatmaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and many consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bacteriocides, plant growth regulators, fertilizers, etc.

Some of the compounds of this invention are useful as herbicides in both pre- and post-emergent applications.

A further understanding of the invention can be had in the following non-limiting Examples. Wherein, unless expressly stated to the contrary, all temperatures and temperature ranges refer to the centigrade system and the term "ambient" or "room temperature" refers to about 20° to 25° C. The term "percent" refers to weight percent and the term "mol" or "mols" refers to gram mols. The term "equivalent" refers to a reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly isomer mixtures are obtained as products.

EXAMPLE 1

Preparation of N-1-methoxycarbonylcyclopropyl-N-methoxymethylcarbonyl-2,6-dimethylaniline 11 gm of methyl 2-(N-methoxyacetyl-2,6-dimethylanilino)-4-chlorobutyrate 0.0335 moles, (the preparation of which is described in U.S. patent application Ser. No. 280,653 and incorporated herein by reference) was added to 125 ml of dimethoxyethane. 1.6 gm of sodium hydride (50% mixture in mineral oil), 0.0335 moles, was added to the system in portions. After addition, the system was stirred at room temperature for 72 hours. The system was then filtered through anhydrous magnesium sulfate. The dimethoxyethane was removed by stripping to give an oil. The oil was crystallized using petroleum ether/ethyl acetate to give 8.5 gm of N-1-methoxycarbonylcyclopropyl-N-methoxymethylcarbonyl-2,6-dimethylaniline as a white crystalline solid, m.p. 68° to 69° C., listed as compound number 5 in Table I.

EXAMPLE 2

Preparation of N-1-methoxycarbonylcyclopropyl-N-prop-2-enylcarbonyl-2,6-dimethylaniline 6.9 gm methyl 2-(N-crotonyl-2,6-dimethylanilino)-4-chlorobutyrate, 0.02 moles (the preparation of which is described in U.S. patent application Ser. No. 280,653 and which is incorporated herein by reference) was added to 150 ml of dimethoxyethane. 1 gm of sodium hydride (50% mixture in mineral oil), 0.02 moles, was added to the system in portions. After addition, the system was stirred at room temperature for 120 hours. The system was filtered through anhydrous magnesium sulfate. The dimethoxyethane was removed by stripping to give an oil. The product was purified by column chromatography using silica gel and a mixture of hexane, ethyl ether and petroleum ether as the eluant. 2.2 gm of N-1-methoxycarbonylcyclopropyl-N-prop-2-enylcarbonyl-2,6-dimethylaniline was recovered as a yellow oil listed as compound number 7 in Table I.

EXAMPLE 3

Preparation of N-1-hydroxycarbonylcyclopropyl-N-methoxymethylcarbonyl-2,6-dimethylaniline 21 gm of N-1-ethoxycarbonylcyclopropyl-N-methoxymethylcarbonyl-2,6-dimethylaniline was dissolved in 125 ml of methanol. 3.5 gm of NaOH in 20 ml water was added to the system. The system was refluxed for 11 hours. Afterwards, the solution was stripped under vacuum. Dichloromethane was added to the residue. Gaseous HCl was bubbled in until a pH of 1 was obtained. At this time a white precipitate fell out of solution. The solution was filtered through magnesium sulfate and the methylene chloride removed by stripping to give the N-1-hydroxycarbonylcyclopropyl-N-methoxymethylcarbonyl-2,6-dimethylaniline as a white solid, m.p. 179°-181° C. listed as compound number 4, Table I.

EXAMPLE 4

Preparation of N-(1-N',N'-dimethylaminocarbonyl-cyclopropyl)-N-methoxymethylcarbonyl-2,6-dimethylaniline 5.5 gm of N-1-hydroxycarbonylcyclopropyl-N-methoxymethylcarbonyl-2,6-dimethylaniline is added to 100 ml of chloroform. The system is cooled to 0° to 5° C. and 2.60 gm of thionyl chloride in 10 ml of chloroform is then slowly added. After addition of the thionyl chloride, the system is stirred at room temperature for 2 hours and is then heated to reflux for an additional hour. The system is then cooled to room temperature and 2.0 gm of anhydrous dimethylamine is slowly added to the system. The system is stirred at room temperature for 2 hours and the reaction is then stopped. The solution is poured into 200 ml of an aqueous acidic solution (pH approximately 2). The product is extracted with chloroform. The chloroform solution is washed with saturated sodium bicarbonate solution and then is dried over magnesium sulfate. The solution is filtered and the chloroform removed by stripping to give the N-(1-N',N'-dimethylaminocarbonylcyclopropyl)-N-methoxymethylcarbonyl-2,6-dimethylaniline.

Other compounds which are prepared in a manner consistent with Examples 1 through 4 above include:

N-1-methoxycarbonylcyclopropyl-N-chloromethylcarbonyl-2,6-dimethylaniline;

N-1-ethoxycarbonylcyclopropyl-N-chloromethylcarbonyl-2,6-dimethylaniline;

N-1-methoxycarbonylcyclopropyl-N-allylcarbonyl-2,6-dimethylaniline;

N-1-methoxycarbonylcyclopropyl-N-prop-2-enylcarbonyl-2,6-dimethylaniline;

N-1-methoxycarbonylcyclopropyl-N-propargylcarbonyl-2,6-dimethylaniline;

N-1-methoxycarbonylcyclopropyl-N-methoxymethylcarbonyl-2-ethyl-6-methylaniline;

N-1-methoxycarbonylcyclopropyl-N-methoxymethylcarbonyl-2-ethylaniline;
N-1-methoxycarbonylcyclopropyl-N-methoxymethylcarbonyl-2-methylaniline;
N-1-ethoxycarbonylcyclopropyl-N-bromomethylcarbonyl-2,6-diethylaniline;
N-1-ethoxycarbonylcyclopropyl-N-methoxymethylcarbonyl-2,6-diethylaniline;
N-1-ethoxycarbonylcyclopropyl-N-methoxymethylcarbonyl-2,6-dimethylaniline;
N-1-methoxycarbonylcyclopropyl-N-methoxymethylcarbonyl-2,6-dimethylaniline;
N-1-methoxycarbonylcyclopropyl-N-hydroxymethylcarbonyl-2,6-dimethylaniline;
N-1-methoxycarbonylcyclopropyl-N-hydroxymethylcarbonylaniline;
N-1-methoxycarbonylcyclopropyl-N-methylthiomethylcarbonyl-2,6-diethylaniline;
N-1-methoxycarbonylcyclopropyl-N-ethylthiomethylcarbonylaniline;
N-(1-N',N'-dimethylaminocarbonylcyclopropyl)-N-methoxymethylcarbonyl-2,6-dimethylaniline;
N-(1-N'-methylaminocarbonylcyclopropyl)-N-methoxymethylcarbonyl-2,6-dimethylaniline;
N-(1-N',N'-diethylaminocarbonylcyclopropyl)-N-chloromethylcarbonyl-2,6-dimethylaniline;
N-(1-N'-ethylaminocarbonylcyclopropyl)-N-methylthiomethylcarbonyl-2,6-diethylaniline;
N-1-hydroxycarbonylcyclopropyl-N-methoxymethylcarbonyl-2,6-dimethylaniline;
N-1-hydroxycarbonylcyclopropyl-N-methylthiomethylcarbonyl-2,6-diethylaniline;
N-1-hydroxycarbonylcyclopropyl-N-chloromethylcarbonyl-2,6-diisopropylaniline;
N-1-hydroxycarbonylcyclopropyl-N-(2-furanylmethylcarbonyl)-2,6-dimethylaniline.

EXAMPLE 5

Tomato Late Blight

Compounds of the invention were tested for the preventative control of the Tomato Late Blight organism *Phytophthora infestans*. Five- to six-week old tomato (cultivar Bonny Best) seedlings were used. The tomato plants were sprayed with a 250 ppm suspension of the test compound in acetone, water and a small amount of a nonionic emulsifier. The sprayed plants were then inoculated one day later with the organism, placed in an environmental chamber and incubated at 66° to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II. In Table II, the test concentration is 250 ppm unless otherwise indicated by the figures in parentheses.

EXAMPLE 6

Celery Late Blight

The celery late blight tests were conducted using celery (Utah) plants 11 weeks old. The celery late blight organism was *Septoria apii*. The celery plants were sprayed with 250 ppm solutions of the candidate toxicant mixed with acetone, water and a nonionic emulsifier. The plants were then inoculated with the organism and placed in an environmental chamber and incubated at 66° to 68° F. in 100% relative humidity for an extended period of time (approximately 48 hours). Following the incubation the plants were allowed to dry and then were maintained in a greenhouse for approximately 14 days. The percent disease control provided by a given candidate toxicant is based on the percent disease reduction relative to untreated check plants. The results are reported in Table II.

EXAMPLE 7

Grape Downy Mildew Control

The compounds of the invention were tested for the control of the grape downy mildew organism *Plasmopara viticola*. Detached leaves, between 70 and 85 mm in diameter, of 7-week old *Vitis vinifera* cultivar Emperor grape seedlings were used as hosts. The leaves were sprayed with a 250 ppm solution of the test compound in acetone. The sprayed leaves were dried, inoculated with a spore suspension of the organism, placed in a humid environmental chamber and incubated at 66° to 68° F. and about 100% relative humidity. After incubation for two days, the plants were then held in a greenhouse seven to nine days; then the amount of disease control was determined. The percent disease control provided by a given test compound was based on the percent disease reduction relative to untreated check plants. The results are tabulated in Table II.

EXAMPLE 8

Tomato Early Blight

Compounds of the invention were tested for the control of the tomato Early Blight organism, *Alternaria solani conidia*. Tomato (variety Bonny Best) seedlings of 6 to 7 weeks old were used. The tomato plants were sprayed with a 250 ppm solution of the test compound in an acetone-and-water solution containing a small amount of a nonionic emulsifier. The sprayed plants were inoculated one day later with the organism, placed in the environmental chamber and incubated at 66° to 68° F. and 100% relative humidity for 24 hours. Following the incubation, the plants were maintained in a greenhouse for about 12 days. Percent diseases control was based on the percent disease development on untreated check plants. The compounds tested and the results are tabulated in Table II.

TABLE I

Compounds of the Formula

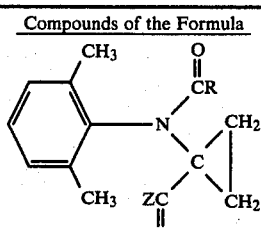

| Compound Number | R | Z | Carbon Calc. | Carbon Found | Hydrogen Calc. | Hydrogen Found | Nitrogen Calc. | Nitrogen Found | Form | m.p. |
|---|---|---|---|---|---|---|---|---|---|---|
| 1 | —$CH_2OCH_3$ | $OC_2H_5$ | 66.88 | 64.34 | 7.57 | 7.84 | 4.59 | 4.60 | yellow oil | |
| 2 | (furyl) | $OCH_3$ | 69.00 | 67.71 | 6.11 | 6.68 | 4.47 | 4.08 | white solid | 130–137° C. |
| 3 | —$CH_2Cl$ | $OCH_3$ | 60.91 | 63.86 | 6.13 | 6.57 | 4.78 | 4.93 | white solid | 94–97° C. |
| 4 | —$CH_2OCH_3$ | OH | 64.97 | 63.75 | 6.91 | 7.02 | 5.05 | 4.93 | white solid | 179–181° C. |
| 5 | $CH_2OCH_3$ | $OCH_3$ | 65.96 | 69.23 | 7.27 | 7.51 | 4.81 | 5.08 | white solid | 68–69° C. |
| 6 | $CH_2CH=CH_2$ | $OCH_3$ | 71.05 | 64.59 | 7.37 | 6.60 | 4.88 | 4.60 | yellow oil | |
| 7 | $CH=CHCH_3$ | $OCH_3$ | 71.05 | 68.76 | 7.37 | 7.29 | 4.87 | 4.41 | yellow oil | |

TABLE II

FUNGICIDAL ACTIVITY % CONTROL

| Compound Number | Grape D.M. | Tom. L.B. | Cel. L.B. | Tom. E.B. |
|---|---|---|---|---|
| 1 | 42 | 29 | 0 | 71 |
| 2 | 37 | 11 | — | 0 |
| 3 | 17 | 0 | 0 | 0 |
| 4 | 8 | 14 | 68 | 11 |
| 5 | 100 | 88 | 0 | 0 |
| 6 | 23 | 18 | 0 | 29 |
| 7 | 11 | 0 | — | 0 |

Grape D.M. - Grape Downy Mildew
Tom. L.B. - Tomato Late Blight
Cel. L.B. - Celery Late Blight
Tom. E.B. - Tomato Early Blight

I claim:

1. A compound of the formula

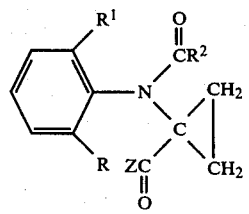

wherein R and $R^1$ are independently hydrogen or lower alkyl; $R^2$ is lower alkenyl, lower alkynyl, or —$CH_2X$ wherein X is halogen, hydroxyl, lower alkoxy, lower alkylthio or a furyl group; Z is hydroxyl, lower alkoxy or —$NR_3R_4$ wherein $R^3$ and $R^4$ are independently hydrogen or lower alkyl.

2. A compound of the formula defined in claim 1 wherein R and $R^1$ are independently lower alkyl.

3. A compound of the formula defined in claim 1 wherein Z is lower alkoxy.

4. A compound of the formula defined in claim 1 wherein $R^2$ is —$CH_2X$
wherein X is halogen, hydroxyl, lower alkoxy, lower alkylthio or an furanyl ring.

5. A compound of the formula defined in claim 4 wherein X is methoxy.

6. A compound of the formula defined in claim 5 wherein R and $R^1$ are methyl.

7. A compound of the formula defined in claim 6 wherein Z is methoxy.

8. A method for the control of fungi which comprises contacting said fungi or their growth environment with a fungicidally effective amount of the compound of the formula defined in claim 1.

9. A fungicidal composition comprising a biologically inert carrier and a fungicidally effective amount of the compound defined in claim 1.

* * * * *